United States Patent [19]

Meddings et al.

[11] 4,344,574

[45] Aug. 17, 1982

[54] CROSS-FLOW NEBULIZER

[75] Inventors: Basil Meddings, Edmonton; Heinz Kaiser, Fort Saskatchewan, both of Canada

[73] Assignee: Sherritt Gordon Mines Limited, Toronto, Canada

[21] Appl. No.: 88,491

[22] Filed: Oct. 26, 1979

[51] Int. Cl.³ .............................................. B05B 7/26
[52] U.S. Cl. ................................. 239/338; 128/200.18
[58] Field of Search ............... 239/338, 343, 432, 542, 239/370, 121, 305; 128/194, 200.18, 200.22

[56] References Cited

U.S. PATENT DOCUMENTS

| | | | |
|---|---|---|---|
| 2,063,397 | 12/1936 | Paschall | 239/338 |
| 2,159,407 | 5/1930 | Seamen et al. | 128/200.18 |
| 3,206,175 | 9/1965 | Boteler | 239/338 |
| 3,842,833 | 10/1974 | Ogle | 128/200.18 |
| 4,049,200 | 9/1977 | Sobol | 239/338 |

Primary Examiner—James B. Marbert
Attorney, Agent, or Firm—Robert F. Delbridge; Arne I. Fors

[57] ABSTRACT

A cross-flow nebulizer is manufactured from first and second deformable tubular members each having a substantially constant external diameter and a central passage of substantially constant diameter extending from a forward end to a rearward end. A forward end portion of each tubular member is deformed to provide the forward end with an orifice of reduced diameter of desired size, and the forward end portions of the tubular members are positioned in an angular spaced relationship with the orifices closely adjacent. The relative positions of the orifices are adjusted to provide a satisfactory spray when gas is passed through one tubular member and the other tubular member is connected to a source of liquid, and the tubular members are integrally connected to maintain the forward ends in the adjusted position.

14 Claims, 6 Drawing Figures

CROSS-FLOW NEBULIZER

This invention relates to cross-flow nebulizers of the kind which are commonly used in spectrometers in which a liquid to be analyzed is introduced in the form of a fine spray. An induction coupled plasma spectrometer is one example of such a spectrometer.

Cross-flow nebulizers of this kind usually comprise two fine hollow glass needles with thin walls and central passages of very small diameter, with the needles having closely spaced, adjacent ends perpendicular to one another. The diameter of the central passages and hence of the orifices at the ends of the needles may for example be about 0.05 mm, and the orifices may be about 0.025 mm apart. A carrier gas such as argon is passed through one needle and the other needle is placed in communication with the liquid to be analyzed, so that the liquid is aspirated from the other needle by the carrier gas in the form of a fine spray which is passed into the spectrometer.

In order to obtain substantially consistent results in the spectrometer, it is necessary to align the needles in a very accurate manner so that the adjacent orifices are very closely and accurately spaced. This is usually carried out by use of a special mechanism and takes a considerably long period of time, for example from one to two hours. In addition to the time taken, there is a constant danger of breaking one or both glass needles during the alignment procedure since they are very fragile. Further, even after alignment, the needles may move out of alignment during use, with movement of only about 0.0125 mm being sufficient to adversely affect the obtaining of satisfactory results in the spectrometer.

It is therefore an object of the invention to provide a method of making an improved nebulizer which overcomes these disadvantages.

According to the invention, a cross-flow nebulizer is made by providing first and second deformable tubular members each having a substantially constant external diameter and a central passage of substantially constant diameter extending from a forward to rearward end, deforming a forward end portion of each tubular member to provide the forward end with an orifice of reduced diameter of desired size, positioning the forward end portions of the tubular members in an angularly spaced relationship with the orifices closely adjacent, adjusting the relative positions of the orifices to provide a satisfactory spray when gas is passed through one tubular member and the other tubular member is connected to a source of liquid, and integrally connecting the members to maintain the forward ends in the adjusted position.

Thus, each tubular member has the desired orifice diameter only at the forward end, and the rearward part of the tubular member is thus considerably stronger than the thin glass needles of the prior art. Also, an orifice of the desired size is readily provided at the forward end by the deforming step. Further, the connection of the first and second tubular members by integral means maintains the orifices in the adjusted position, and thus the regular time-consuming alignments required with the prior art needles are no longer required.

The present invention therefore enables a cross-flow nebulizer to be produced with very small, closely spaced orifices and which overcomes the problems found in prior cross-flow nebulizers of the kind required for the production of sprays for spectrographic analysis.

The first and second tubular members may be ductile, and the deforming step may comprise drawing the forward end portion of each tubular member to cause the external diameter and the diameter of the passage to taper to the forward end, and removing a forward end part of the tapering portion to provide the forward end with the orifice of desired size.

The second tubular member may be provided with a portion which extends substantially parallel to the first tubular member when the orifices are in the adjusted position, with the integral connection being made between the substantially parallel portions of the two members.

The integral connection may be made by fusing first and second bridge sections to the first and second tubular members respectively, adjusting the forward ends to the adjusted position, and fusing the first and second bridge sections together.

The first and second tubular members may be glass tubes, although materials such as suitable metals or synthetic plastics may be used.

The first and second tubular members may have a main external diameter from about 5 mm to about 7 mm with a central passage diameter of from about 0.5 mm to about 1.0 mm, with the forward ends of the tubular members having an external diameter of from about 1 mm to about 3 mm and an orifice diameter of from about 0.02 mm to about 0.4 mm and the forward ends may be spaced apart by a distance of from about 0.01 mm to about 0.15 mm.

Advantageously, the forward end portions of the tubular members are positioned in substantially perpendicular relationship to provide the satisfactory spray, and a flat is provided on the forward end portion of at least one tubular member adjacent the forward end to enable the forward end portions of the tubular members to be positioned closely adjacent one another.

One embodiment of the invention will now be described, by way of example, with reference to the accompanying drawings, in which.

Figure 1:
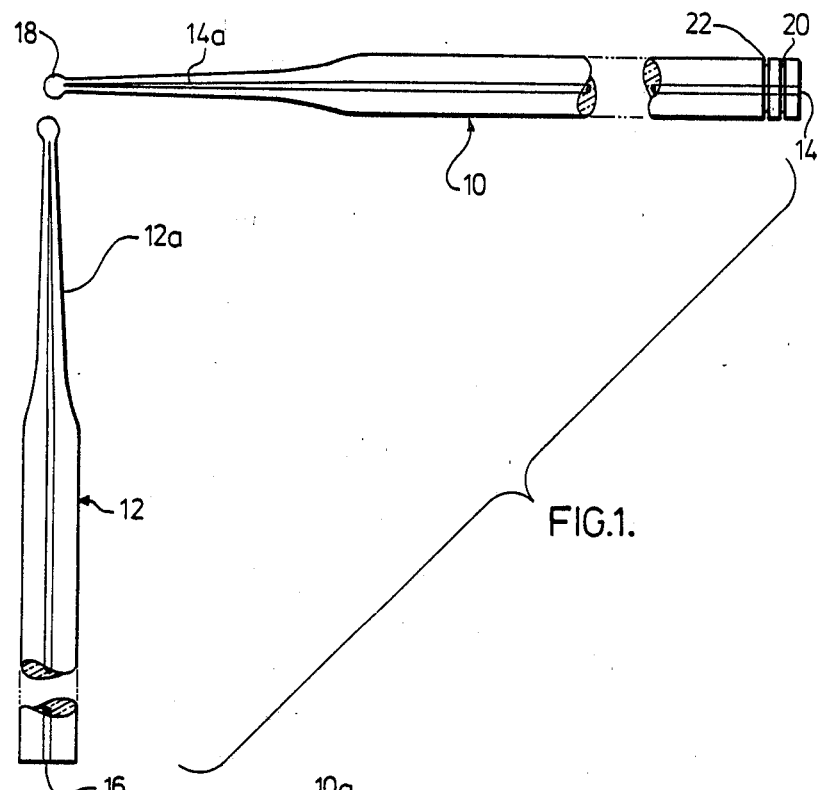
FIGS. 1 to 3 are side views of first and second glass capillary tubes showing various steps in the manufacture of a cross-flow nebulizer in accordance with a preferred embodiment in the invention.

Referring to the drawings, a cross-flow nebulizer is made from two thick-walled glass capillary tubes 10, 12 of 6 mm constant external diameter from end to end and with a central passage 14, 16 respectively of constant 0.5 mm diameter from end to end, the first tube 10 being approximately 10 cm long and the second tube 12 being approximately 4 cm long.

The first end portion 10a of the first glass tube 10 is heated over a glass blowing torch and is drawn to a cone about 10 mm long with a tip diameter of 1.0 to 1.5 mm, as shown in FIG. 1, so that the central passage 14a tapers in diameter to zero at the tip 18. The rear end of the tube 10 is then cut off to give a tube length of 10 cm, and two circumferential grooves 20, 22 are ground in the exterior of the tube at 5 mm and 7 mm respectively from the cut end, which is then fire-polished over a glass blowing torch.

A steel wire (not shown) of 0.127 mm diameter is inserted into the open rear end of the tube 10 until it contacts the interior of the tapering passage 14a. The tip 18 is cut off at a distance of 2 mm from the end of the wire, and the wire is withdrawn. The tube 10 is connected at its rear end to a 200 psi argon supply via a mass flow meter which continuously monitors the flow of argon through the tube 10. The front end is ground and polished with a miniature grinding tool mounted under a stereo microscope until the mass flow meter shows an argon flow of from 500 to 520 milliliters/min. This flow rate corresponds to a passage diameter of 0.065 mm at the orifice 24 at the front end 26 of the tube 10.

Figure 2:
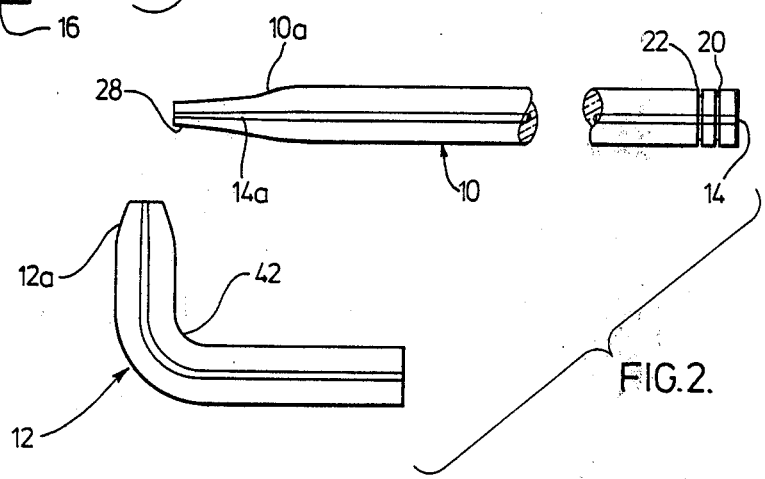
Figure 5:
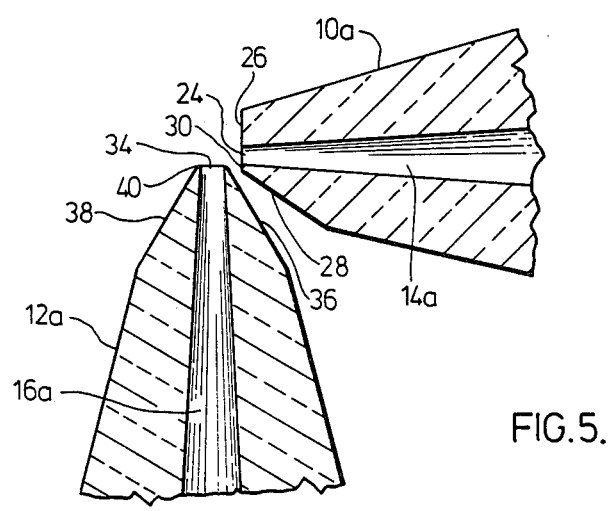
FIG. 5 is an enlarged view of the forward end portions of the nebulizer tubes.

By means of a similar micro-grinding process, a flat 28 (see FIG. 2) is produced on the forward end portion 10a adjacent the front end 26 to remove a sector-shaped section therefrom. The flat 28 is formed by grinding at an angle of 30° to the longitudinal axis of the tube 10, with the distance between the sector line 30 and the orifice 24 being less than the diameter of the orifice 24 (see FIG. 5).

Figure 3:
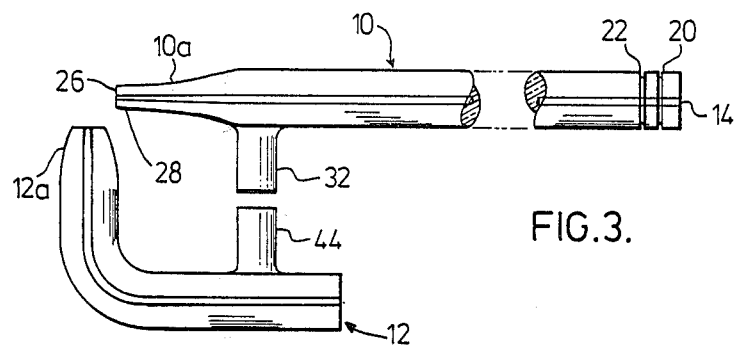

A glass rod 32 of 7 mm length and 3 mm diameter (see FIG. 3) is integrally connected by conventional glass connecting technique to the tube 10 at a distance of 12 mm from the front end, that is to say just rearwardly of the tapering front end portion 10a, so that the rod 32 extends perpendicularly to the longitudinal axis of the tube 10 in alignment with the flat 28.

The second glass tube 12 is then treated in a similar manner to the first glass tube 10, except that the final length is 3.5 cm, no external grooves are provided, an 0.25 mm wire is used for rough-sizing the orifice, and the final size of the orifice 34 at the front end is 0.20 mm. Also, two diametrically opposed flats 36, 38 are ground on the tapering front end portion 12a to form a front end 40 of chisel-shape with sharp edges on opposite sides of the orifice 34.

The tube 12 is bent through 90° at a location 42 which is 13 mm from the tip 40, and a glass rod 44 about 6 mm in length and 3 mm in diameter is integrally connected with the tube 12 at a position where it is aligned with the glass rod 32 attached to the other tube 10 when the orifices 24, 34 of the two tubes 10, 12 are close to each other.

The second tube 12 is connected with a liquid source (not shown) by means of a flexible plastic tube 46 (shown in FIG. 6) connected to the rear end of the tube 12 by an appropriate adapter 48, and the first tube 10 is similarly connected to a 200 psi argon gas supply, with sealing rings 50, 52 first being fitted in the annular grooves 20, 22 in the tube 10. The tubes 10, 12 are mounted in a jig (not shown) so that the tapering end portions 10a, 12a are spaced apart and perpendicular to one another with the orifices 24, 34 closely adjacent to each other, with the tube 12 being fixedly mounted in the jig and the tube 10 being mounted for movement in three mutually perpendicular directions relative to the tube 12.

When the gas-emitting orifice 24 is moved close to the orifice 34 in communication with the liquid, the high pressure argon jet creates suction in the tube 12 so that liquid is aspirated up the tube 12 to the orifice 34. When the liquid reaches the orifice 34, the argon jet from the orifice 24 shears the liquid into fine droplets, thereby generating a fine mist. Small vertical, horizontal and lateral adjustments are made to the position of the gas orifice 24 relative to the liquid orifice 34 until the mist becomes a straight well-defined spray, the aspiration rate of liquid is approximately 1.5 milliliters per minute as can be measured with a graduated cylinder and stop watch, and the spray contains a minimum proportion of large droplets. In this last respect, the droplet size can be judged effectively by impinging the mist onto the graticule of a measuring magnifier and observing the droplets adhering to the graticule.

Figure 4:
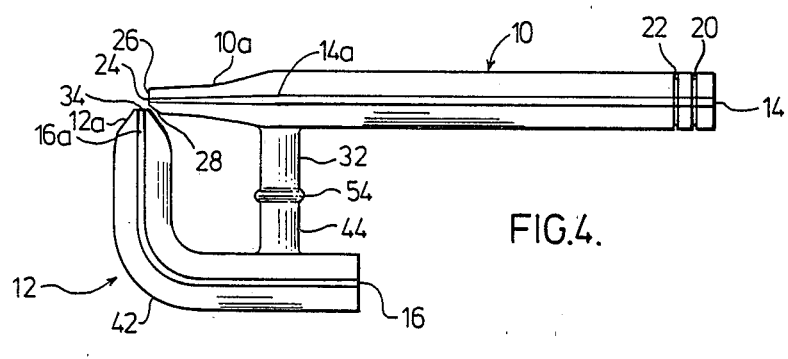
FIG. 4 is a similar view of the completed cross-flow nebulizer.

When the optimum position of the orifice 24 has been achieved, a micro-welding technique is used to fuse the glass rods 32, 44 together at 54, thereby forming an integral connection between the tubes 10, 12 to maintain the orifices 24, 34 in the set position (see FIG. 4). The spacing between the orifices 24, 34 will then be from 0.010 mm to 0.15 mm.

Figure 6:
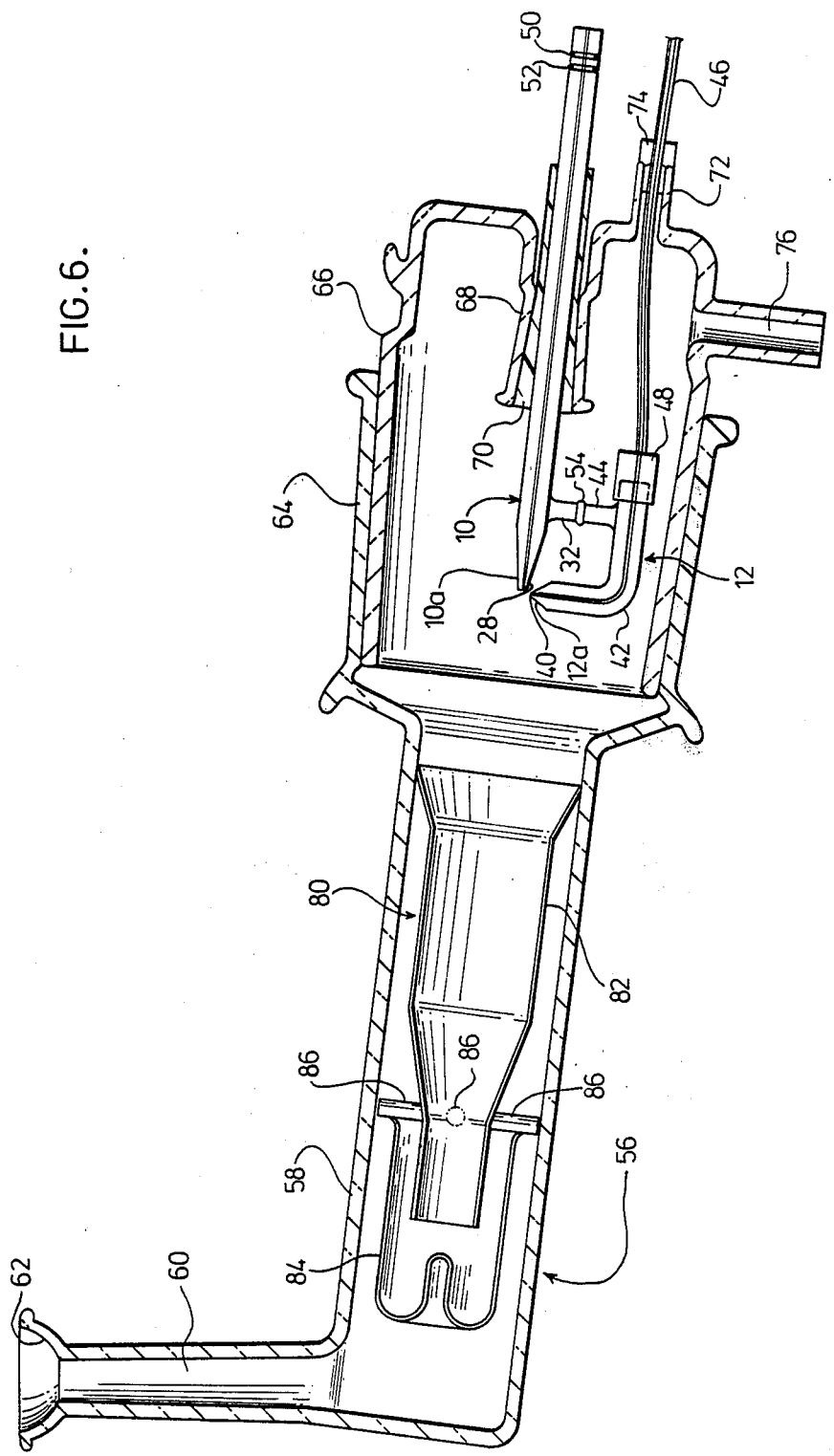
FIG. 6 is a side view of the nebulizer fitted into an expansion chamber from which the spray is passed to an induction coupled argon plasma spectrometer.

As shown in FIG. 6, the nebulizer of the present invention can be utilized by fitting it into an expansion chamber 56 at the spray inlet of an induction-coupled argon plasma spectrometer. The expansion chamber has a slightly inclined cylindrical glass body 58 with a vertical outlet passage 60 terminating in a ball joint socket 62 by means of which the chamber 58 is fitted to a spectrometer in known manner. The inlet 64 of the body 58 receives a hollow open-ended glass stopper 66 having a central cylindrical inlet 68 in which the tube 10 of the nebulizer is secured by a wedge-shaped annular adapter 70. The liquid carrying tube 46 extends from the stopper 66 through a cylindrical passage 72 closed by a plug 74. The stopper 66 also has a drain outlet 76. Between the nebulizer and the outlet passage 60, the cylindrical body 58 contains a glass baffle 80. The baffle 80 has a first cylindrical portion 82 through which spray passes from the nebulizer into a second cup-like portion 84 of larger diameter than the adjacent end of the cylindrical portion 82. The open end of the cup-like portion 84 is secured to the cylindrical portion 82 by four mutually perpendicular glass rods 86 which also serve to centrally locate that end of the baffle 80 in the body 58. The other end of the baffle is located in the body 58 by the opposite end of the first portion 82.

The spray from the nebulizer thus passes through the first cylindrical portion 82, makes a first 180° turn to exit from the second cup-like portion 84 and then makes a second 180° turn to pass between the body 58 and the cup-like portion 84 to the outlet passage 60. The baffle 80 serves to remove large droplets from the spray. Due to the inclination of the body 58, liquid formed from such droplets ultimately drains away through drain outlet 76.

The function of the expansion chamber 58 will be clear to a person skilled in the art and hence it is not necessary to explain this function in detail other than to mention that, in use, the spray from the nebulizer passes through the body 58 and baffle 80 and into the spectrometer through the vertical outlet passage 60.

The advantages of the present invention will be readily apparent to a person skilled in the art from the above description of the preferred embodiment. As mentioned earlier, the thick-walled glass capillary tubes 10, 12 are much stronger than the fine thin-walled glass needles of the prior art nebulizers. The integral connection of the glass rods 32, 44 maintains the orifices 24, 34 in the predetermined relationship, thus obviating the necessity of the time-consuming alignment and re-alignment required by the prior art. Further, orifices 24, 34 of the desired size can readily be produced in the manner described.

Although the tubes are made of glass in the preferred embodiment, it is within the scope of the invention to make the tubes of other suitable materials, for example a suitable metal such as stainless steel or suitable synthetic plastic material.

Also, more than one liquid-supply tube 12 may be integrally connected to the gas-supply tube 10 to increase the sensitivity of the spectrometer. For example, up to four equi-angularly spaced liquid-supply tubes 12 may be provided, with further appropriate flats 28 being provided on the gas-supply tube 10.

Other embodiments within the scope of the invention will be apparent to a person skilled in the art, the scope of the invention being defined in the appended claims.

What we claim as new and desire to protect by Letters Patent of the United States is:

1. A method of making a cross-flow nebulizer comprising providing first and second deformable glass tubular members each having a substantially constant external diameter and a central passage of substantially constant diameter extending from a forward end to a rearward end, said external diameter being from about 5 mm to about 7 mm and said passage diameter being from about 0.5 mm to about 1.0 mm, deforming a forward end portion of each tubular member to provide the forward end with an orifice of reduced diameter from about 0.02 mm to about 0.4 mm, positioning the forward end portions of the tubular members in an angular spaced relationship with the orifices closely adjacent, connecting one tubular member to a source of liquid and passing a gas through the other tubular member to cause a spray to be emitted from said one tubular member, adjusting the relative positions of the orifices to a spacing from about 0.01 mm to about 0.15 mm to provide a satisfactory spray, and integrally connecting the glass tubular members by fusion to maintain the forward ends in the adjusted position.

2. A method according to claim 1 wherein the deforming step comprises drawing the forward end portion of each tubular member to cause the external diameter and the diameter of the passage to taper to the forward end, and removing a forward end part of the tapering portion to provide the forward end with the orifice of desired size.

3. A method according to claim 1 wherein the second tubular member is provided with a portion which extends parallel to the first tubular member when the forward ends are in the adjusted position, and the integral connection is made between substantially parallel portions of the tubular members.

4. A method according to claim 1 wherein the integral connection is made by fusing first and second glass bridge sections to the first and second tubular members respectively, adjusting the forward ends to the adjusted position, and fusing the first and second bridge sections together.

5. A method according to claim 1 wherein the forward end portions of the tubular members are positioned in substantial perpendicular relationship.

6. A method according to claim 1 including providing a flat adjacent the forward end of the forward end portion of at least one tubular member to enable the forward ends of the tubular members to be positioned closely adjacent one another.

7. A method according to claim 1 including providing a flat on the forward end portion of one tubular member to form a sharp edge on that side of the orifice opposite the other tubular member.

8. A cross-flow nebulizer comprising first and second glass tubular members each having a central passage extending from a forward end to a rear end and each having a deformed forward end portion providing a forward end with an orifice of reduced predetermined size, each tubular member having a main portion rearwardly of the forward end portion with a substantially constant external diameter and a substantially constant passage diameter, said external diameter being from about 5 mm to about 7 mm, said central passage having a diameter from about 0.5 mm to about 1.0 mm and said orifice having a diameter of from about 0.02 mm to about 0.4 mm, the forward end portions of the first and second tubular members being in a fixed angularly spaced relationship with the orifices spaced apart by a distance of from about 0.01 mm to about 0.15 mm, and glass means integrally fused to the first and second tubular members to maintain the forward ends of the first and second tubular members in the predetermined relationship.

9. A cross-flow nebulizer according to claim 8 wherein the deformed forward end portion of each tubular member is a drawn forward end portion, with an external diameter and the passage diameter tapering to the forward end.

10. A cross-flow nebulizer according to claim 8 wherein the second tubular member has a portion which extends substantially parallel to the first tubular member and the integral means extends between substantially parallel portions of the tubular member.

11. A cross-flow nebulizer according to claim 9 wherein the integral means comprises a bridge member extending between a portion of the first tubular member adjacent the forward end portion and a portion of the second tubular member substantially parallel thereto.

12. A cross-flow nebulizer according to claim 8 wherein the forward end portions of the tubular members are in substantially perpendicular relationship.

13. A cross-flow nebulizer according to claim 8 wherein the forward end portion of at least one tubular member has a flat adjacent the forward end permitting the forward end portions of the tubular members to be closely adjacent one another.

14. A cross-flow nebulizer according to claim 8 wherein the forward end portion of one tubular member has a flat providing a sharp edge on that side of the orifice opposite the other tubular member.

* * * * *